United States Patent [19]

Elnagar

[11] Patent Number: 5,565,600

[45] Date of Patent: Oct. 15, 1996

[54] ALKYL-AROMATIC DIPHOSPHITES

[75] Inventor: Hassan Y. Elnagar, Baton Rouge, La.

[73] Assignee: Albemarle Corporation, Richmond, Va.

[21] Appl. No.: 494,989

[22] Filed: Jun. 26, 1995

Related U.S. Application Data

[63] Continuation of Ser. No. 358,057, Dec. 16, 1994, abandoned, which is a continuation of Ser. No. 122,440, Sep. 24, 1993, abandoned, which is a continuation-in-part of Ser. No. 674,462, Mar. 25, 1991, abandoned.

[51] Int. Cl.$^6$ .................................................. C07F 9/02
[52] U.S. Cl. ........................................................... 558/74
[58] Field of Search .............................. 252/400.24, 401, 252/403; 524/119; 558/74

[56] References Cited

U.S. PATENT DOCUMENTS

| | | | |
|---|---|---|---|
| 3,192,243 | 6/1965 | Gagliani | 524/120 |
| 3,737,485 | 6/1973 | Hechenbleikner | 524/119 |
| 3,873,498 | 3/1975 | Brunetti | 524/119 |
| 4,305,866 | 12/1981 | York et al. | 524/119 |
| 4,584,331 | 4/1986 | Tamura et al. | 524/119 |

FOREIGN PATENT DOCUMENTS 9216537  10/1992  WIPO .................................... 558/74

OTHER PUBLICATIONS

Mukmeneva et al. "Synthesis of Pentaerythritol diphosphites with enhanced stability to hydrolysis", Journal of General Chemistry of the USSR, vol. 57, No. 12, part 2, Dec. 1987. pp. 2494–2495.

Journal of General Chemistry of the USSR, vol. 57, No. 12, part 2, Dec. 1987, N. A. Mukmeneva et al. "Synthesis of Pentaerythritol diphosphites with enhanced stability to hydrolysis", pp. 2795–2797.

Primary Examiner—Kriellion S. Morgan
Attorney, Agent, or Firm—Philip M. Pippenger

[57] ABSTRACT

Novel alkyl-aromatic diphosphites having antioxidant and flame-retarding abilities and corresponding to the formula:

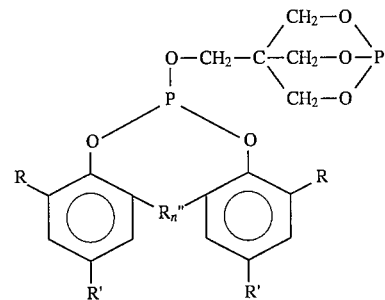

can be prepared by reacting a 2,2'-bridged bisphenol corresponding to the formula:

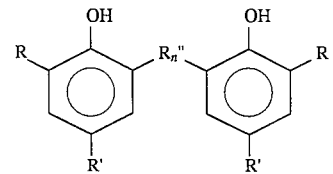

with pentaerythritol dichlorophosphite at 20–150° C. in the presence of a basic catalyst; R and R' in the formulas representing hydrocarbyl groups, R" being a divalent bridging group, and n being 0 or 1. These diphosphites have good hydrolytic stability per se and can be made even more resistant to hydrolysis by stabilizing them with at least 0.5% by weight of an acid scavenger, preferably before they are recovered from their synthesis reaction mixtures.

8 Claims, No Drawings

ALKYL-AROMATIC DIPHOSPHITES

This application is a continuation of application Ser. No. 08/358,057, filed Dec. 16, 1994, abandoned, which is a continuation of Ser. No. 08/122,440, filed Sep. 24, 1993, now abandoned, which in turn is a continuation-in-part of Ser. No. 07/674,462, filed Mar. 25, 1991, now abandoned.

FIELD OF INVENTION

This invention relates to alkyl-aromatic diphosphites which have a cyclic caged structure and which have utility as antioxidants, stabilizers, and flame retardants for organic materials.

BACKGROUND

As disclosed in U.S. Pat. No. 3,808,296 (Bruneni), 3,927,150 (Schwarzenbach et al.), U.S. Pat. No. 4,305,866 (York et al.), and U.S. Pat. No. 4,371,647 (Minagawa et al.), it is known that many phosphorus compounds, including some aromatic phosphites having a cyclic caged structure, have been found to be useful as stabilizers for organic materials which are normally susceptible to oxidative deterioration and that they are frequently particularly useful in this regard when employed in conjunction with phenolic antioxidants.

It is also known, however, that some phosphites have been discovered to be unsatisfactory for use as antioxidants because of lacking good overall stabilizing ability, contributing color to polymeric materials in which they have been incorporated, and/or being thermally or hydrolytically unstable.

Kirpichnikov et al., *Russian Chemical Reviews*, Vol. 52 (11), 1983, pp. 1051–1063, teach that effective stabilization of polymers can be achieved by the use of synergistic mixtures of phosphites having different types of activity, i.e., inhibition of radical processes (a sterically-hindered aromatic phosphite) and serving as an acceptor of molecular polymer reaction products (aliphatic and mixed alkyl aryl phosphites).

In a different field of endeavor, phosphorus compounds are of interest as potential replacements for halogen compounds as flame retardants for normally flammable organic materials because of the hazards involved in the use of the halogen compounds. Known phosphorus compounds have been found to be generally inferior to the halogen compounds, especially the bromine compounds, which have been the flame retardants of choice for many organic polymers; and it would therefore be advantageous to discover new phosphorus compounds which might be superior to the known phosphorus compounds in this regard.

SUMMARY OF INVENTION

It has now been found that novel alkyl-aromatic diphosphites having antioxidant and flame-retarding abilities and corresponding to the formula:

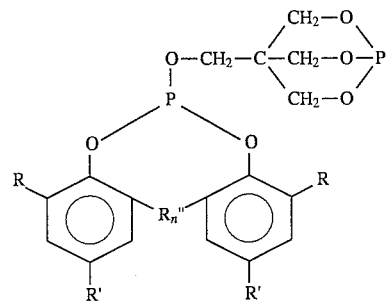

can be prepared by reacting a 2,2'-bridged bisphenol corresponding to the formula:

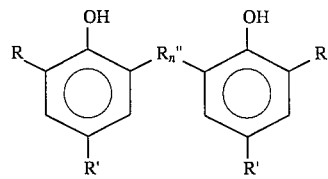

with pentaerythritol dichlorophosphite at 20°–150° C. in the presence of a basic catalyst; R and R' in the formulas representing hydrocarbyl groups, R" being a divalent linking group, and n being 0 or 1.

The novel diphosphites have different degrees of hydrolytic stability but consistently have better resistance to hydrolysis than commercial diphosphites, and they can be provided with even greater hydrolytic stability by combining them with acid scavengers before or after they are recovered from their synthesis reaction mixtures.

DETAILED DESCRIPTION

The 2,2'-bridged bisphenols which can be used to prepare the novel diphosphites are compounds in which (1) the bridge at the 2,2'-position is provided by a direct bond between the benzene rings or by a divalent bridge, e.g., a sulfur, sulfoxide, sulfone, or alkylidene bridge, generally an alkylidene group containing 1–18 carbons, such as a methylene, ethylidene, propylidene, butylidene, isobutylidene, pentylidene, hexylidene, octylidene, or decylidene bridge, and (2) the hydrocarbyl groups which are ortho and para to the hydroxy groups may be the same or different and may be, e.g., alkyl groups such as methyl, ethyl, propyl, isopropyl, butyl, t-butyl, pentyl, or hexyl; cycloalkyl groups such as cyclohexyl, cyclooctyl, or cyclodecyl; and/or aromatic groups such as phenyl, tolyl, or benzyl.

The bisphenols having an ethylidene bridge are sometimes preferred because of the particularly good degree of hydrolytic stability exhibited by the diphosphites prepared from them, and it is also apt to be preferred for the hydrocarbyl substituents on the rings to be alkyl groups containing 1–6 carbons. However, satisfactory diphosphites are also obtained from the other bisphenols.

In the preparation of the alkyl-aromatic diphosphites, the bisphenols may be reacted with pentaerythritol dichlorophosphite that is formed in situ; but it is preferred to react the bisphenols with preformed pentaerythritol dichlorophosphite, since the latter reaction is both faster and cleaner.

When a preformed pentaerythritol dichlorophosphite is to be used, it may be a compound that has been recovered from its synthesis reaction mixture, i.e., the reaction mixture in which it was prepared. However, it is preferably an unisolated compound; and the synthesis of the alkyl-aromatic diphosphite is effected by (1) adding the appropriate bisphenol to the pentaerythritol dichlorophosphite-containing reaction mixture resulting from the reaction of pentaerythritol with phosphorus trichloride at 20°–150° C. in the presence of a basic catalyst and (2) maintaining contact between the bisphenol and pentaerythritol dichlorophosphite at 20°–150° C. until the alkyl-aromatic diphosphite is formed.

Pentaerythritol dichlorophosphite is conveniently prepared by adding phosphorus trichloride to pentaerythritol in a suitable organic solvent and allowing reaction to occur at 20°–150° C., preferably 35°–45° C., and most preferably at the reflux temperature of the reaction mixture, in an inert atmosphere, such as nitrogen, in the presence of a basic catalyst. Either reactant may be used in excess without preventing the formation of the desired product, but it is preferred to employ the reactants in substantially stoichiometric amounts, i.e., in a phosphorus trichloride/pentaerythritol mol ratio of about 2/1.

Although the solvent used in the process does not appear to be critical, it is preferred to use a common organic solvent, e.g., an aliphatic or aromatic hydrocarbon, such as hexanes, benzene, toluene, or xylene, or a halogenated hydrocarbon, such as chlorobenzene, methylene chloride, or chloroform. Methylene chloride is especially preferred.

Utilizable basic catalysts include, e.g., alkali metal amides, such as sodium or lithium amide. However, the preferred basic catalysts are tert-amines. Any of the tert-amines conventionally employed as basic catalysts may be used, including, e.g., triethylamine, tributylamine, triphenylamine, and phenyldimethylamine. The preferred tert-amines, however, are quinoline, pyridine, and alkylpyridines, especially pyridine.

Whether the pentaerythritol dichlorophosphite is preformed or formed in situ, the alkyl-aromatic diphosphite synthesis is conducted by combining the appropriate bisphenol with pentaerythritol dichlorophosphite or with pentaerythritol and phosphorus trichloride in a suitable organic solvent, such as those mentioned above, and allowing reaction to occur at 20°–150° C., preferably 40°–50° C., and most preferably at the reflux temperature of the reaction mixture, in the presence of a basic catalyst, such as those mentioned above.

As in the pentaerythritol dichlorophosphite synthesis, the preferred solvent for use in the alkyl-aromatic diphosphite synthesis is methylene chloride, the preferred catalyst is pyridine, and the reactants are preferably employed in substantially stoichiometric amounts, i.e., in a bisphenol/pentaerythritol dichlorophosphite mol ratio of about 1/1. However, the desired alkyl-aromatic diphosphite can also be prepared when either reactant is employed in excess of the stoichiometric amount even when the bisphenol and pentaerythritol dichlorophosphite are utilized in the 2/1 mol ratio that would be expected to lead to the formation of a compound corresponding to the formula:

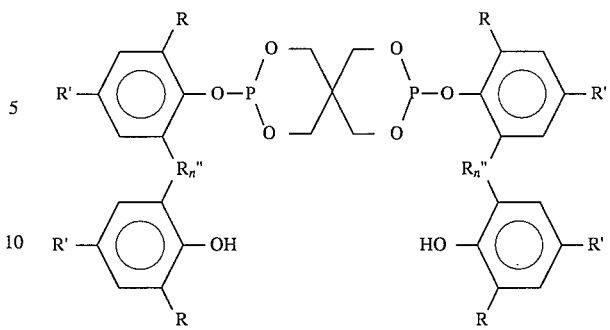

Actually, of course, it is surprising that the alkyl-aromatic diphosphites of the invention could be prepared from the reactants in any tool ratio, since (1) a diphosphite having a spiro structure, such as that shown above, is the product one would expect to obtain when a phenol and pentaerythritol dichlorophosphite are reacted in any proportions. (2) Example 4 of U.S. Pat. No. 3.192,243 (Gagliani) shows that such a spiro structure has previously been obtained even when the phenol has been a bisphenol, and (3) rearrangement into the cyclic caged structure could not have been predicted.

After completion of the bisphenol/pentaerythritol dichlorophosphite reaction, the alkyl-aromatic diphosphite product may be recovered by conventional means; and it is preferably crystallized one or more times from a suitable solvent, such as isopropanol, to provide a purer product.

The diphosphites of the invention are diphosphites which have a cyclic caged structure and contain both an aliphatic phosphite structure and a mixed alkyl-aryl phosphite structure in a single molecule. They have good thermal and hydrolytic stability and can be effectively used as antioxidants or stabilizers for organic materials which are normally susceptible to oxidative deterioration (including, e.g., discoloration and molecular degradation) and/or as flame retardants for normally flammable organic materials without unduly discoloring the organic materials.

Organic materials which may benefit from the incorporation of the novel diphosphites as antioxidants and/or flame retardants include natural polymers, such as cellulose, rubber, and their derivatives, e.g., cellulose acetate, propionate, or butyrate or methyl cellulose, as well as the many synthetic polymers which are known to be normally susceptible to oxidative deterioration and/or to be normally flammable. Among these synthetic polymers are:

(1) polymers and interpolymers of ethylenically-unsaturated hydrocarbons, such as ethylene, propylene, butylene, isobutylene, 4-methyl-1-pentene, styrene, butadiene, and piperylene, including the homopolymers, the copolymers, and other interpolymers thereof with one another, and the copolymers and interpolymers of at least one of them with one or more copolymerizable non-hydrocarbons, such as vinyl acetate, acrylonitrile, methacrylonitrile, methyl acrylate, and methyl methacrylate, (2) halogen-containing polymers, such as polyvinyl chloride and fluoride, polyvinylidene chloride, vinyl chloride-vinylidene chloride copolymers, polychloroprene, and chlorinated rubbers, (3) other vinyl and allyl polymers, such as polyvinyl alcohol, acetate, stearate, benzoate, maleate, and butyral, polyallylmelamine, and polyallyl phthalate, (4) acrylic polymers, such as polyacrylates, polymethacrylates, polyacrylamides, polyacrylonitrile, and polymethacrylonitrile, and (5) various other polymers, such as epoxy polymers, polycarbonates, polyurethanes, polyureas, polyamides, polyesters, polyethers, polysulfones, phenol-formaldehyde resins, urea-formaldehyde resins, and melamine-formaldehyde resins.

In a preferred embodiment of the invention, the organic material is a polyethylene, polypropylene, polystyrene, ABS (acrylonitrile-butadiene-styrene terpolymer), polyalkylene terephthalate, or polycarbonate composition which, like the other polymeric compositions that may be modified in accordance with the invention, may contain one or more of the ingredients conventionally employed in such compositions, such as light stabilizers (e.g., hindered amine light stabilizers), ultraviolet light absorbers, metal deactivators, pigments, dyes, lubricants, nucleation agents, and fillers.

The alkyl-aromatic diphosphites are combined with the organic materials by any suitable technique known for the incorporation of phosphites into organic materials. The amount incorporated may be a flame-retardant amount, generally 0.05–15%, preferably 0.1–1.5%, based on the weight of the normally flammable organic material; or an antioxidant amount, generally 0.005–5%, preferably 0.01–2%, based on the weight of the organic material which is normally susceptible to oxidative deterioration.

When used as an antioxidant, the alkyl-aromatic diphosphite may be used alone or in combination with a phenolic antioxidant, which, when employed, is used in an antioxidant amount, such as the antioxidant amounts mentioned above, and which may be any of the sterically-hindered phenols known to be effective as antioxidants, such as 2,6-di-t-butyl-4-methylphenol, 2,6-di-t-butyl-4-methoxymethylphenol, 2,2'-ethylidene-bis(4,6-di-t-butylphenol), 4,4'-thiobis(2-methyl-6-t-butylphenol), and the many other known phenolic antioxidants. A particularly preferred phenolic antioxidant for use with the novel diphosphitesis 1,3,5-trimethyl-2,4,6-tris(3,5-di-t-butyl-4-hydroxybenzyl)-benzene.

Also sometimes useful for use in conjunction with the diphosphites are thioester synergists, such as dilauryl thiodipropionate and distearyl thiodipropionate.

Although the diphosphites of the invention have good hydrolyric stability per se, it has been found that they can be made even more resistant to hydrolysis by stabilizing them with at least 0.5% by weight of an acid scavenger, based on the weight of the diphosphite. The acid scavengers may be blended with the diphosphites after they have been recovered from their synthesis mixtures, just as the stabilizers of U.S. Pat. No. 4,402,858 (Capolupe et al.) and European Patent Application 0 400 454 (Enlow et al.) are blended with the different phosphites of those publications to stabilize them against hydrolysis during storage and later use. However, it can be even more advantageous to blend them with the diphosphites before recovering the diphosphites from their synthesis reaction mixtures.

The reason it can be preferable to effect admixture of an acid scavenger and diphosphite before allowing the diphosphite to crystallize from its synthesis reaction mixture is that decomposition of the diphosphite by hydrolysis can occur even before it is recovered from the reaction mixture, especially when a crystallization solvent is employed in the recovery. As in the recovery of other organophosphorus compounds, it is apt to be preferred to recover the novel diphosphites with the aid of a crystallization solvent which is relatively inexpensive, easy to handle, and low in toxicity. However, many of the crystallization solvents which might be preferred for those properties, e.g., acetonitrile, and alcohols, such as methanol, ethanol, 1-propanol, 2-propanol, 2-butanol, and t-butanol, can lead to decomposition of organophosphorus compounds via hydrolysis and/or transesterification during recovery processes utilizing them. Incorporation of an acid scavenger into the synthesis reaction mixture before the diphosphite is allowed to crystallize minimizes such decomposition and thus can increase the yield and purity of the product as well as stabilizing the diphosphite against hydrolysis during storage and later use.

The acid scavenger used to stabilize the diphosphite may be any compound capable of scavenging the acidic residues present in the diphosphite as prepared. However, it is preferably a metal carboxylate, oxide, or carbonate, such as a lithium, sodium, potassium, copper, zinc, cadmium, magnesium, calcium, barium, aluminum, or other metal carbonate, oxide, or salt of a carboxylic acid, e.g., a carboxylic acid containing 6–20 carbons, such as hexanoic, heptanoic, octanoic, decanoic, dodecanoic, tetradecanoic, hexadecanoic, stearic, or eicosanic acid; or an alkanolamine, such as ethanolamine or triisopropanolamine. Among the particularly preferred stabilizers are calcium stearate, triisopropanolamine, zinc oxide, sodium carbonate, magnesium aluminum hydroxy carbonates, and the magnesium aluminum carbonate compositions known as talcites and hydrotalcites.

When an acid scavenger is employed to stabilize a diphosphite of the invention, the amount used is at least 0.5%, preferably at least 1%, based on the weight of the diphosphite. Even greater stabilization can sometimes be achieved with larger amounts of the acid scavenger, but it is seldom necessary to utilize more than 5% of the acid scavenger to achieve essentially complete prevention of acidic decomposition. Thus, the amount of acid scavenger used is most commonly in the range of 0.5–10%, preferably 1–5%, based on the weight of the diphosphite.

The following examples are given to illustrate the invention and are not intended as a limitation thereof. Unless other, vise specified, quantities mentioned in the examples are quantities by weight.

EXAMPLE 1

Preparation of AN-1169

Charge a suitable reaction vessel with 99.8 mmols of pentaerythritol, 100 mL of methylene chloride, and 12.3 mmols of pyridine. Add 200 mmols of $PCl_3$ quickly, and maintain the mixture under a nitrogen atmosphere. Heat the mixture to about 40° C. As the reaction proceeds, neutralize the generated HCl with a caustic scrubber. After one hour, when the reaction mixture becomes completely clear, add 105 mmols of 2,2'-ethylidenebis(4,6-di-t-butylphenol) in one portion, and continue heating at about 44° C. overnight. Recover the product and crystallize it from 400 mL of isopropanol. Dry the crystallized product to provide 45 g (72% yield) of a white solid having a melting point of 291°–295° C. Spectral analyses (H-NMR, P-NMR, and IR) confirm the identity of the solid as 2,2'-ethylidenebis(4,6-di-t-butylphenyl)-methylene-(2",6",7"-trioxa-1-phosphabicyclo-[2.2.2]-octanyl)phosphite.

EXAMPLE 2

Preparation of AN-1170

Repeat the reaction of Example 1 except for substituting 119.8 mmols of 2,2'-methylenebis( 6-t-butyl-4-methylphenol) for the bisphenol charge of that example and then continuing the heating for 5.7 hours. At the end of the reaction, dilute the slurry with 150 mL of methylene chloride, purge the reaction mixture with ammonia to precipitate ammonium chloride, remove the ammonium chloride by filtration, add the filtrate to 120 mL of isopropanol, and distill off the methylene chloride under reduced pressure. Filter the resulting slurry and dry under vacuum to provide 46.4 g (87.4%) of a white solid having a melting point of 233° C. Spectral analyses confirm the identity of the solid as 2,2'-methylenebis(6-t-butyl-4-methylphenyl)-methylene(2",6",7"-trioxa-1-phosphabicyclo-[2.2.2]-octanyl)phosphite.

EXAMPLE 3

Preparation of AN-1171

Repeat the reaction of Example 1 except for substituting 110 mmols of 2,2'-methylenebis( 4,6-di-t-butylphenol) for the bisphenol charge of that example and then continuing the heating for two hours, after which most of the solvent has evaporated and a white slurry is obtained. Discontinue heating, and recover and purify the product as in Example 2 to provide 41 g (67%) of a white solid which is identified by spectral analyses as 2,2'-methylenebis(4,6-di-t-butylphenyl)-methylene-(2",6",7"-trioxa-1 -phosphabicyclo-[2.2.2]-octanyl)phosphite.

When this example is essentially repeated except for doubling the amount of bisphenol so as to use two molar equivalents instead of one, only one of the molar equivalents enters into the reaction, and the same product is formed.

EXAMPLE 4

Preparation of AN-1172

Repeat the reaction of Example 1 except for substituting 117 mmols of 2,2'-isobutylidenebis( 4,6-dimethylphenol) for the bisphenol charge of that example and then heating at about 62° C. for 45 minutes, after which most of the methylene chloride has evaporated and the mixture has become a thick slurry. Add 100 mL of methylene chloride to redissolve the solidfying mixture, bubble ammonia gas through the solution to form ammonium chloride, and separate the ammonium chloride by filtration. Add 150 mL of isopropanol to the clear filtrate, distill off methylene chloride, filter the resultant slurry, and dry to provide 29 g (59%) of a product which has a melting point of 186°–188° C. and is identified by spectral analyses as 2,2'-isobutylidenebis(4,6-dimethylphenyl)-methylene-(2",6",7"-trioxa-1-phosphabicyclo-[2.2.2]-octanyl)phosphite.

EXAMPLE 5

Preparation of AN-1174

Repeat the reaction of Example 1 except for substituting 112.8 mmols of 2,2'ethylidenebis(6-t-butyl-4-methylphenol) for the bisphenol charge of that example and then continuing the hearing at 60° C. for four hours, after which the reaction mixture has become a thick slurry. Then discontinue heating, add 100 mL of methylene chloride, purge with ammonia, filter, remove the methylene chloride, dissolve the residue in 100 mL of pentane, and leave the solution to crystallize overnight. Filter the product, wash with cold pentane, and dry under reduced pressure to provide 35 g (64% yield) of white crystals which have a melting point of 243°–248° C. and are identified by spectral analyses as 2,2'-ethylidenebis(6-t-butyl-4-methylphenyl)-methylene( 2",6",7"-trioxa-1-phosphabicyclo-[2.2.2]-octanyl)phosphite.

EXAMPLE 6

Preparation of AN-1182

Charge a suitable reaction vessel with a slurry of 99.8 mmols of pentaerythritol and 199.6 mmols of $PCl_3$ in 100 mL of methylene chloride, add 1.0 mL of pyridine, and heat the mixture so that a gentle reflux is maintained. Apply a slightly positive pressure of nitrogen atmosphere, and neutralize the generated HCl with a caustic scrubber as the reaction proceeds. After 30 minutes, when the reaction mixture becomes completely clear, quickly add 119 mmols of 2,2'-methylidenebis(6-t-butyl-4-ethylphenol) and continue heating for four hours.

Discontinue heating, dilute the reaction mixture with 200 mL of methylene chloride, and bubble ammonia through the diluted reaction mixture to neutralize any excess HCl and precipitate ammonium chloride. Add 300 mL of isopropanol, distill off methylene chloride under reduced pressure, cool the resulting slurry, filter, and dry to provide 40.5 g (72.5%) of a white solid having a melting point of 233.3°–235.3° C. Spectral analyses confirm the identity of the product as 2,2'-methylidenebis(6-t-butyl-4-ethylphenyl)-methylene-(2",6",7"-trioxa-1-phosphabicyclo-[2.2.2]-octanyl)phosphite.

EXAMPLE 7

Preparation of Stabilized AN-1182

Repeat Example 6 except for adding 0.5% of calcium stearate, based on the weight of diphosphite, prior to crystallization.

EXAMPLE 8

Preparation of AN-1185

Repeat the reaction of Example 6 except for substituting 111.6 mmols of 2,2'-thiobis( 6-t-butyl-4-methylphenol) for the bisphenol charge of that example and then continuing heating for 3.5 hours. Add an additional 10 mL of pyridine to complete the reaction, also add 100 mL of methylene chloride, and continue heating for another two hours. Purge the reaction mixture with ammonia, filter, and crystallize the product from 200 mL of isopropanol to provide 16.6 g of a white solid having a melting point of 187.9°–194.3° C. Spectral analyses confirm the identity of the solid as 2,2'-thiobis(6-t-butyl-4-methylphenyl)-methylene-(2",6",7"-trioxa-1-phosphabicyclo-[2.2.2]-octanyl)phosphite.

EXAMPLE 9

Preparation of AN-1187

Repeat the reaction of Example 6 except for substituting 109.8 mmols of 2,2'-decylidenebis( 2,4-dimethylphenol) for the bisphenol charge of that example and then continuing the heating for 1.5 hours. After an ammonia work-up, followed by filtration to remove ammonium chloride, crystallize the product twice from 100 mL of isopropanol to provide 22.9 g (40%) of a white solid having a melting point of 145.1°–146.9° C. Spectral analyses confirm the identity of the product as 2,2'-decylidenebis(4,6-dimethylphenyl)-methylene-(2",6",7"-trioxa-1-phosphabicyclo-[2.2.2]-octanyl)phosphite.

EXAMPLE 10

Preparation of AN-1193

Charge a suitable reaction vessel with a slurry of 50 mmols of pentaerythritol and 100 mmols of $PCl_3$ in 50 mL of methylene chloride, add 1.0 mL of pyridine, and heat the mixture so that a gentle reflux is maintained. Apply a slightly positive pressure of nitrogen atmosphere, and neutralize the generated HCl with a caustic scrubber as the reaction proceeds. After 30 minutes, when the reaction mixture becomes clear, add 50 mmols of 2,2'-butylidenebis(4,6-dimethylphenol) and continue heating for four hours. After cooling to room temperature, dilute the reaction mixture with 100 mL of methylene chloride, purge with ammonia for 20 minutes, and filter to remove solid ammonium chloride. Add 100 mL of isopropanol, remove methylene chloride under reduced pressure, filter, and dry to provide 16.5 g (67.3%) of a white solid having a melting point of 175°–177.8° C. Spectral analyses confirm the identity of the product as 2,2'-butylidenebis(4,6-dimethylphenyl)-methylene-(2",6",7"-trioxa-1-phosphabicyclo-[2.2.2]-octanyl)phosphite.

EXAMPLE 11

Preparation of AN-1199

Repeat the reaction of Example 10 except for heating the reaction mixture for 70 minutes before adding a bisphenol, substituting 55 mmols of 2,2'-methylenebis(4,6-dimethylphenol) for the bisphenol of that example, and then continuing the heating for 1.5 hours. After diluting the reaction mixture with 100 mL of methylene chloride, purging with ammonia, filtering, and adding 100 mL of isopropanol, add 0.5 g of DHT-4C (an anhydrous talcite sold by Kyowa Chemical Industry) to neutralize any acid trace. Then filter the mixture and distill off methylene chloride to provide 10.2 g of white product, and allow the filtrate to stand overnight to provide a second crop (4.2 g)—a total yield of 64%. Spectral analyses confirm the identity of the product as 2,2'-methylenebis( 4,6-dimethylphenyl)-methylene-(2",6",7"-trioxa-1-phosphabicyclo-[2.2.2]-octanyl)phosphite.

EXAMPLE 12

Hydrolytic Stability Testing

Part A

Dissolve 560 mg of the AN-1182 of Example 6 in 5.0 mL of a 95/5 mixture of tetrahydrofuran and water. Maintain the solution at room temperature under nitrogen and monitor it periodically by gas chromatography (GC) to determine the extent of hydrolysis of the AN-1182. The test results are shown in Table I.

Part B

Repeat Part A except for replacing the AN-1182 of Example 6 with the calcium stearate-stabilized AN-1182 of Example 7 (AN-1182/CaSt). The test results are shown in Table I.

TABLE I

| Diphosphite | GC Area % of Hydrolysis Products | | | |
|---|---|---|---|---|
| | AN-1182 | | AN-1182/CaSt | |
| Days | Bisphenol | HP[1] | Bisphenol | HP[1] |
| 0 | 1.2 | — | 1.0 | 0.2 |
| 1 | 3.0 | 1.3 | ND[2] | ND[2] |
| 3 | ND[2] | ND[2] | 4.2 | — |
| 4 | 48.0 | 41.1 | 9.4 | 3.1 |
| 5 | 51.3 | 44.3 | 16.9 | 9.4 |
| 6 | * | * | 45.5 | 19.7 |
| 7 | | | 51.7 | 42.2 |
| 8 | | | 69.8 | 27.4 |
| 9 | | | * | * |

[1]HP = hydrogen phosphonate
[2]ND = not determined
*No testing because of completion of hydrolysis the previous day

EXAMPLE 13

Hydrolytic Stability Testing

Dissolve five 560 mg samples of the AN-1182 of Example 6 in 5.0 mL of a 95/5 mixture of tetrahydrofuran and water, and add 5.5 mg of a stabilizer to each of the solutions—the stabilizers being, respectively, zinc oxide, calcium stearate, triisopropanolamine (TIPA), sodium carbonate, and DHT-4C. Maintain the solutions at room temperature under nitrogen and monitor them periodically by gas chromatography (GC) to determine the extent of hydrolysis of the AN-1182. The test results are shown in Table II.

TABLE II

| | GC Area % of Unchanged Diphosphite | | | | |
|---|---|---|---|---|---|
| Days | ZnO | CaSt | TIPA | $Na_2CO_3$ | DHT-4C |
| 3 | 98 | 81 | 98 | 97 | 98 |
| 4 | 95 | 52 | ND[1] | 96 | ND[1] |
| 5 | 97 | 4 | 96 | 97 | 97 |
| 6 | ND[1] | 0 | ND[1] | ND[1] | ND[1] |
| 7 | 96 | | 95 | 97 | 97 |
| 11 | 97 | | 60 | 96 | 97 |
| 13 | ND[1] | | 0 | ND[1] | ND[1] |
| 31 | 96 | | | 95 | 96 |

[1]ND = not determined

EXAMPLE 14

Testing of Diphosphites as Antioxidants

Part A

Prepare four blends of polypropylene powder and 0.01% of calcium stearate as an acid neutralizer and lubricant. Retain one of the blends (Blend A) as a control, and modify the others by blending therewith 0.1% of the following diphosphites:

| Blend | Diphosphite |
|---|---|
| B | AN-1187 |
| C | AN-1182 |
| D | AN-1185 |

Part B

Test the compositions of Part A for melt flow index and yellowness index by extruding them in a Brabender twin screw extruder at 150°–245°–245° C. and 30 rpm under nitrogen and then making five passes through a Brabender single screw extruder at 260°–260°–260° C. and 30 rpm with ambient air. The test results are shown in Table III.

TABLE III

| Blend | AN-# | MFI @ 230° C./2160 g Load Extrusion Passes | | | | Yellowness Index Extrusion Passes | | |
|---|---|---|---|---|---|---|---|---|
| | | TwS | ss1 | ss3 | ss5 | ss1 | ss3 | ss5 |
| A | none | 8.6 | 13.2 | 39.4 | — | 5.4 | 6.8 | — |
| B | 1187 | 3.5 | 5.0 | 8.1 | 12.9 | 4.3 | 5.3 | 6.2 |
| C | 1182 | 3.1 | 4.3 | 6.7 | 9.5 | 5.1 | 6.0 | 7.5 |
| D | 1185 | 3.0 | 4.8 | 7.1 | 8.9 | 4.1 | 5.0 | 5.8 |

EXAMPLE 15

Testing of Diphosphites with Phenolic as Antioxidants

Part A

Prepare six blends of polypropylene powder containing 0.05% of 1,3,5-trimethyl- 2,4,6-tris(3,5-di-t-butyl-4-hydroxybenzyl)benzene and 0.01% of calcium stearate. Retain one of the blends (Blend E) as a control, and modify the others by blending therewith 0.05% of the following diphosphites:

| Blend | Diphosphite |
|---|---|
| F | AN-1174 |
| G | AN-1169 |
| H | AN-1172 |
| I | AN-1170 |
| J | AN-1171 |

Part B

Test the compositions of Part A for melt flow index and yellowness index as in Example 14 except for using temperatures of 175°–280°–280° C. in the twin screw extruder. The test results are shown in Table IV.

TABLE IV

| Blend | AN-# | MFI @ 230° C./2160 g Load Extrusion Passes | | | | Yellowness Index Extrusion Passes | | |
|---|---|---|---|---|---|---|---|---|
| | | TwS | ss1 | ss3 | ss5 | ss1 | ss3 | ss5 |
| E | none | 4.3 | 6.5 | 11.3 | 17.7 | 4.5 | 5.9 | 7.0 |
| F | 1174 | 3.8 | 4.2 | 5.8 | 7.3 | 4.1 | 4.7 | 5.3 |
| G | 1169 | 3.4 | 3.8 | 5.5 | 7.3 | 3.7 | 4.6 | 6.0 |
| H | 1172 | 3.4 | 3.7 | 5.3 | 7.2 | 4.0 | 5.5 | 6.3 |
| I | 1170 | 3.2 | 4.0 | 5.0 | 6.8 | 4.1 | 4.9 | 6.3 |
| J | 1171 | 3.3 | 3.8 | 5.7 | 6.6 | 4.2 | 4.8 | 6.2 |

I claim:

1. A process which comprises reacting a 2,2'-bridged bisphenol corresponding to the formula:

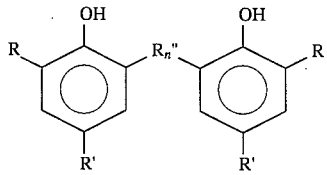

with pentaerythritol dichlorophosphite at 20°–150° C. in the presence of a basic catalyst to form a 2,2'-bridged alkyl-aromatic diphosphite corresponding to the formula:

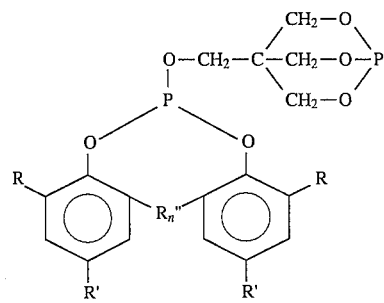

in which formulas R and R' are hydrocarbyl groups selected from the group consisting of alkyl, cycloalkyl, and aromatic groups; R" is a divalent group selected from the group consisting of sulfur, sulfoxide, sulfone, and $C_1$–$C_{18}$ alkylidene groups; n is 0 or 1; and the 2,2'-bridge is a direct bond between the rings when n is 0 and a divalent R" group when n is 1.

2. The process of claim 1 wherein the basic catalyst is a tert-amine.

3. The process of claim 2 wherein the tert-amine is pyridine.

4. The process of claim 1 wherein the pentaerythritol dichlorophosphite that is reacted with the 2,2'-bridged bisphenol is preformed by reacting pentaerythritol with phosphorus trichloride at 20°–150° C. in the presence of the basic catalyst.

5. The process of claim 4 wherein the 2,2'-bridged bisphenol is added to the pentaerythritol dichlorophosphite-containing reaction mixture resulting from the pentaerythritol/phosphorus trichloride reaction, and the temperature is maintained at 20°–150° C. until the alkyl-aromatic diphosphite is formed.

6. The process of claim 1 wherein the 2,2'-bridged bisphenol is initially mixed with pentaerythritol and phosphorus trichloride at 20°–150° C. in the presence of the basic catalyst so that the pentaerythritol dichlorophosphite reactant is formed in situ.

7. The process of claim 1 wherein at least 0.5% by weight of an acid scavenger, based on the weight of the alkyl-aromatic diphosphite, is added to the reaction mixture before the diphosphite is recovered therefrom.

8. The process of claim 7 wherein the acid scavenger is selected from alkanolamines and metal carboxylates, oxides, and carbonates and is added in an amount such as to constitute at least 1%, based on the weight of the diphosphite.

* * * * *